US00PP32913P3

(12) United States Plant Patent
Barnes

(10) Patent No.: US PP32,913 P3
(45) Date of Patent: Mar. 23, 2021

(54) ***PETUNIA* PLANT NAMED 'BBTUN22503'**

(50) Latin Name: ***Petunia* X *hybrida***
Varietal Denomination: BBTUN22503

(71) Applicant: Brent D. Barnes, Riverside, CA (US)

(72) Inventor: Brent D. Barnes, Riverside, CA (US)

(73) Assignee: PLANT 21 LLC, Bonsall, CA (US)

( * ) Notice: Subject to any disclaimer, the term of this patent is extended or adjusted under 35 U.S.C. 154(b) by 0 days.

(21) Appl. No.: 16/873,588

(22) Filed: May 14, 2020

(65) Prior Publication Data

US 2020/0367403 P1 Nov. 19, 2020

(30) Foreign Application Priority Data

May 17, 2019 (CA) ..... PBR 19-9876

(51) Int. Cl.
*A01H 5/02* (2018.01)
*A01H 6/82* (2018.01)

(52) U.S. Cl.
USPC ..... Plt./356.12
CPC ..... *A01H 6/824* (2018.05)

(58) Field of Classification Search
USPC ..... Plt./263.1, 356.1, 356.12
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct *Petunia* plant named 'BBTUN22503', characterized by its upright to outwardly spreading and mounding to eventually trailing plant habit; vigorous growth habit and rapid growth rate; freely branching habit; dense and bushy plant form; early and freely flowering habit; double-type flowers that are dark red purple and white in color; and excellent garden performance.

1 Drawing Sheet

Botanical designation: *Petunia* X *hybrida*.
Cultivar denomination: 'BBTUN22503'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9876. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Petunia* plant, botanically known as *Petunia* X *hybrida* and hereinafter referred to by the name 'BBTUN22503'.

The new *Petunia* plant is a product of a planned breeding program conducted by the Inventor in Bonsall, Calif. The objective of the breeding program is to create new vigorous, freely-branching and uniformly mounding *Petunia* plants with early and freely flowering habit, attractive double-type flowers and good garden performance.

The new *Petunia* plant originated from a cross-pollination made by the Inventor on Oct. 16, 2013 in Bonsall, Calif. of *Petunia* X *hybrida* 'USTUNJ2401', disclosed in U.S. Plant Pat. No. 28,028, as the female, or seed, parent with *Petunia* X *hybrida* 'Sundasiro', disclosed in U.S. Plant Pat. No. 20,870, as the male, or pollen, parent. The new *Petunia* plant was discovered and selected by the Inventor as a single flowering plant within the progeny of the stated cross-pollination in a controlled greenhouse environment in Bonsall, Calif. on Jun. 18, 2014.

Asexual reproduction of the new *Petunia* plant by vegetative terminal cuttings in a controlled greenhouse environment in Bonsall, Calif. since Jun. 27, 2014 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBTUN22503'. These characteristics in combination distinguish 'BBTUN22503' as a new and distinct *Petunia* plant:

1. Upright to outwardly spreading and mounding to eventually trailing plant habit.
2. Vigorous growth habit and rapid growth rate.
3. Freely branching habit; dense and bushy plant form.

4. Early and freely flowering habit.
5. Double-type flowers that are dark red purple and white in color.
6. Excellent garden performance.

Plants of the new *Petunia* can be compared to plants of the female parent, 'USTUNJ2401'. In side-by-side comparisons, plants of the new *Petunia* differ primarily from plants of 'USTUNJ2401' in the following characteristics:

1. Plants of the new *Petunia* are more vigorous than and not as compact as plants of 'USTUNJ2401'.
2. Plants of the new *Petunia* have double-type flowers that are dark red purple and white in color whereas plants of 'USTUNJ2401' have single-type flowers that are red purple and white in color.
3. Plants of the new *Petunia* perform better in the garden than plants of 'USTUNJ2401'.

Plants of the new *Petunia* can be compared to plants of the male parent, 'Sundasiro'. In side-by-side comparisons, plants of the new *Petunia* differ primarily from plants of 'Sundasiro' in the following characteristics:

1. Plants of the new *Petunia* are more outwardly spreading and not as upright as plants of 'Sundasiro'.
2. Plants of the new *Petunia* have double-type flowers that are dark red purple and white in color whereas plants of 'USTUNJ2401' have double-type flowers that are white in color.
3. Plants of the new *Petunia* perform better in the garden than plants of 'Sundasiro'.

Plants of the new *Petunia* can be compared to plants of 'KL 1117', disclosed in U.S. Plant Pat. No. 25,485. In side-by-side comparisons, plants of the new *Petunia* differ primarily from plants of 'KL 1117' in the following characteristics:

1. Plants of the new *Petunia* are more outwardly spreading than and not as upright as plants of 'KL 1117'.
2. Plants of the new *Petunia* have double-type flowers that are dark red purple and white in color whereas plants of 'KL 1117' have single-type flowers that are white in color.
3. Plants of the new *Petunia* perform better in the garden than plants of 'KL 1117'.

Plants of the new *Petunia* can also be compared to plants of 'Kakegawa S36', disclosed in U.S. Plant Pat. No. 14,037. In side-by-side comparisons, plants of the new *Petunia* differ primarily from plants of 'Kakegawa S36' in the following characteristics:

1. Plants of the new *Petunia* are more mounding than plants of 'Kakegawa S36'.
2. Plants of the new *Petunia* are more freely branching and denser than plants of 'Kakegawa S36'.
3. Plants of the new *Petunia* have double-type flowers that are dark red purple and white in color whereas plants of 'Kakegawa S36' have single-type flowers that are magenta in color.
4. Plants of the new *Petunia* have stronger pathogen tolerance and perform better in the garden than plants of 'Kakegawa S36'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

At the top of the photographic sheet (FIG. 1) is a side perspective view of a typical flowering plant of 'BBTUN22503' grown in a container and at the bottom of the photographic sheet is a close-up view of a typical flowering plant of 'BBTUN22503'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Petunia* production. During the production of the plants, day temperatures averaged 27° C. and night temperatures averaged 15° C. Plants were pinched three weeks after planting and were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Petunia* X *hybrida* 'BBTUN22503'.

Parentage:

*Female, or seed, parent.*—*Petunia* X *hybrida* 'USTUNJ2401', disclosed in U.S. Plant Pat. No. 28,028.

*Male, or pollen, parent.*—*Petunia* X *hybrida* 'Sundasiro', disclosed in U.S. Plant Pat. No. 24,520.

Propagation:

*Type.*—Terminal vegetative cuttings.

*Time to initiate roots, summer.*—About three to four days at ambient temperatures ranging from 17° C. to 29° C.

*Time to initiate roots, winter.*—About five to seven days at ambient temperatures ranging from 17° C. to 21° C.

*Time to produce a rooted plant, summer.*—About three weeks at ambient temperatures ranging from 17° C. to 29° C.

*Time to produce a rooted plant, winter.*—About four weeks at ambient temperatures ranging from 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading and mounding to eventually trailing plant habit; freely branching habit with about eight primary lateral branches each with about ten secondary branches developing per plant, dense and bushy plant form; pinching enhances development of lateral branches; vigorous growth habit and rapid growth rate.

*Plant height.*—About 22.6 cm.

*Plant diameter* (*area of spread*).—About 56.8 cm.

*Lateral branches.*—Length: About 21.1 cm. Diameter: About 2.7 mm. Internode length: About 2.5 cm.

Strength: Moderately strong; flexible, not brittle. Aspect: Initially upright then outwardly spreading to almost horizontal. Texture and luster: Densely pubescent; matte. Color, developing: Close to 144B. Color, developed: Close to 137B.

Leaf description:

*Arrangement*.—Alternate before flowering; opposite after flowers develop; leaves simple.

*Length*.—About 6.1 cm.

*Width*.—About 2.5 cm.

*Shape*.—Elliptic.

*Apex*.—Acute.

*Base*.—Cuneate.

*Margin*.—Entire, not undulate.

*Texture and luster, upper and lower surfaces*.—Moderately pubescent; matte.

*Venation pattern*.—Pinnate, arcuate.

*Color*.—Developing leaves, upper surface: Close to 138A. Developing leaves, lower surface: Close to 138B. Fully developed leaves, upper surface: Close to N137D; venation, close to 144B. Fully developed leaves, lower surface: Close to 147B; venation, close to 145B.

*Petioles*.—Length: About 1.1 cm. Diameter: About 2 mm. Strength: Strong, flexible. Texture and luster, upper and lower surfaces: Densely pubescent; matte. Color, upper surface: Close to 145A to 145B. Color, lower surface: Close to 145B.

Flower description:

*Flower type and flowering habit*.—Double terminal and axillary salverform flowers; flowers face mostly upward to outwardly; freely flowering habit with about 170 flower buds and open flowers per plant at one time.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About five to seven days; flowers not persistent.

*Fragrance*.—None detected.

*Flower buds*.—Length: About 2.6 cm. Diameter: About 7 mm. Shape: Oblong, elongate. Texture and luster: Pubescent; matte. Color, sepals: Close to 137B. Color, petals: Close to N92A; distally, close to 83B.

*Flower diameter*.—About 3.8 cm.

*Flower depth* (*height*).—About 3.4 cm.

*Tube length*.—About 2.1 cm.

*Tube diameter, distally*.—About 9 mm.

*Tube diameter, proximally*.—About 2 mm.

*Petals*.—Quantity and arrangement: Five petals fused in a single salverform whorl. Petal lobe length (from throat): About 1.2 cm. Petal lobe width: About 1.7 cm. Petal lobe shape: Spatulate. Petal lobe apex: Broadly obtuse. Petal lobe margin: Entire; moderately undulate. Petal lobe texture and luster, upper surface: Smooth, glabrous; velvety; matte. Petal lobe texture and luster, lower surface: Slightly to moderately pubescent; matte. Tube texture and luster: Slightly to moderately pubescent; matte. Color: When opening, upper surface: More purple than N74A. When opening, lower surface: Close to N78C; towards the margins, close to 85D. Fully opened, upper surface: More purple than N74A; towards the margins, close to NN155D; towards the base, close to 83C to 83D; venation, similar to lamina or close to 187C; with development, main color becoming closer to N74C. Fully opened, lower surface: Close to N78C; towards the margins, close to NN155D; venation, similar to lamina or close to N144A; with development, main color becoming closer to N74C to N74D. Flower tube (outside): Close to N77B to N77C; venation, close to 144B.

*Petaloids*.—Quantity and arrangement: About ten to twelve fused in two whorls. Petal lobe length (from throat): About 3.7 cm. Petal lobe width: About 2.2 cm. Petal lobe shape: Irregular. Petal lobe apex: Broadly acute. Petal lobe margin: Entire; strongly undulate. Petal lobe texture and luster, upper surface: Smooth, glabrous; velvety; matte. Petal lobe texture and luster, lower surface: Smooth, glabrous; matte. Tube texture and luster: Slightly to moderately pubescent; matte. Color: When opening and fully opened, upper surface: More purple than N74A; venation, close to N74A and N78C; with development, color becoming closer to N74C. When opening and fully opened, lower surface: Close to N78D; venation, close to N78D; with development, color becoming closer to N74C to N74D.

*Sepals*.—Quantity and arrangement: Five sepals fused in a single star-shaped whorl. Length: About 1.2 cm. Width: About 2 mm. Shape: Narrowly oblong. Apex: Obtuse. Margin: Entire. Texture and luster, upper surface: Sparsely to moderately pubescent; matte. Texture and luster, lower surface: Moderately pubescent; matte. Color: When opening and fully developed, upper surface: Close to N137D. When opening and fully developed, lower surface: Close to 137B.

*Peduncles*.—Length: About 3.3 cm. Width: About 1.5 mm. Strength: Moderately strong to strong; wiry and flexible, not brittle. Angle: About 45° from stem axis. Texture and luster: Densely pubescent; matte. Color: Close to 144A.

*Reproductive organs*.—Stamens: Quantity per flower: About eight to ten. Filament length: About 1.3 cm. Filament color: Close to 157B. Anther length: About 2 mm. Anther shape: Bi-lobed. Anther color: Close to 97D. Pollen amount: Moderate. Pollen color: Close to 91C. Pistils: Quantity per flower: One. Pistil length: About 1.8 cm. Style length: About 1.7 cm. Style color: Close to 145C; distally, close to N187A. Stigma diameter: About 2 mm. Stigma shape: Round. Stigma color: Close to 148A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1° C. to about 40° C.

It is claimed:

1. A new and distinct *Petunia* plant named 'BBTUN22503' as illustrated and described.

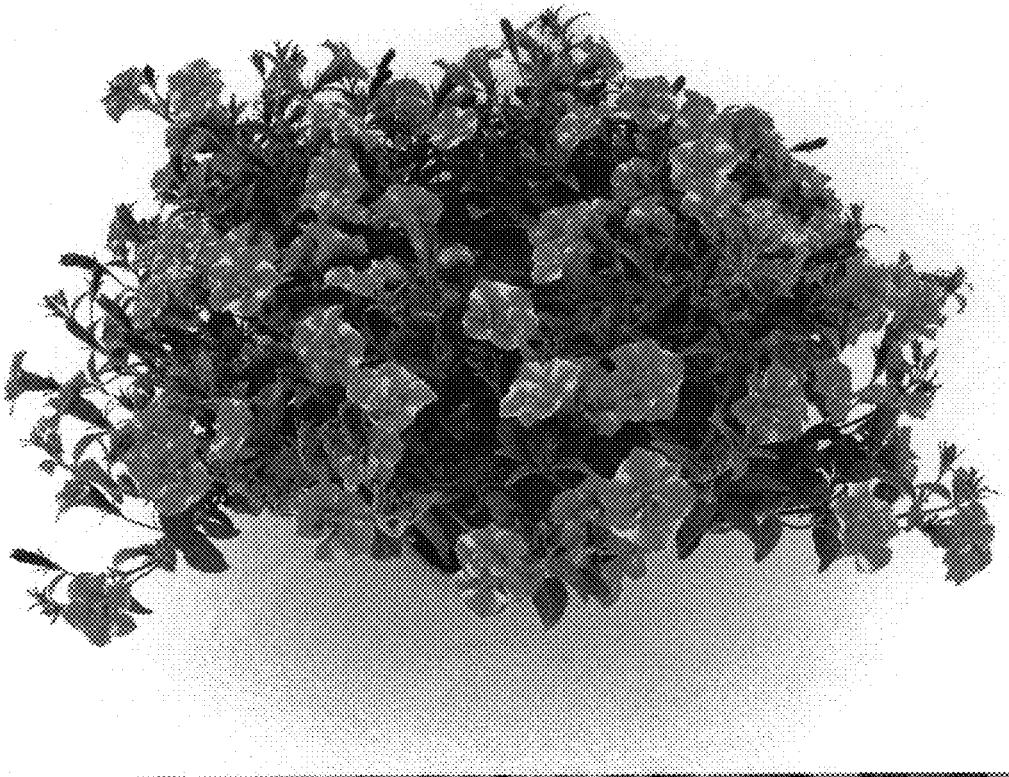
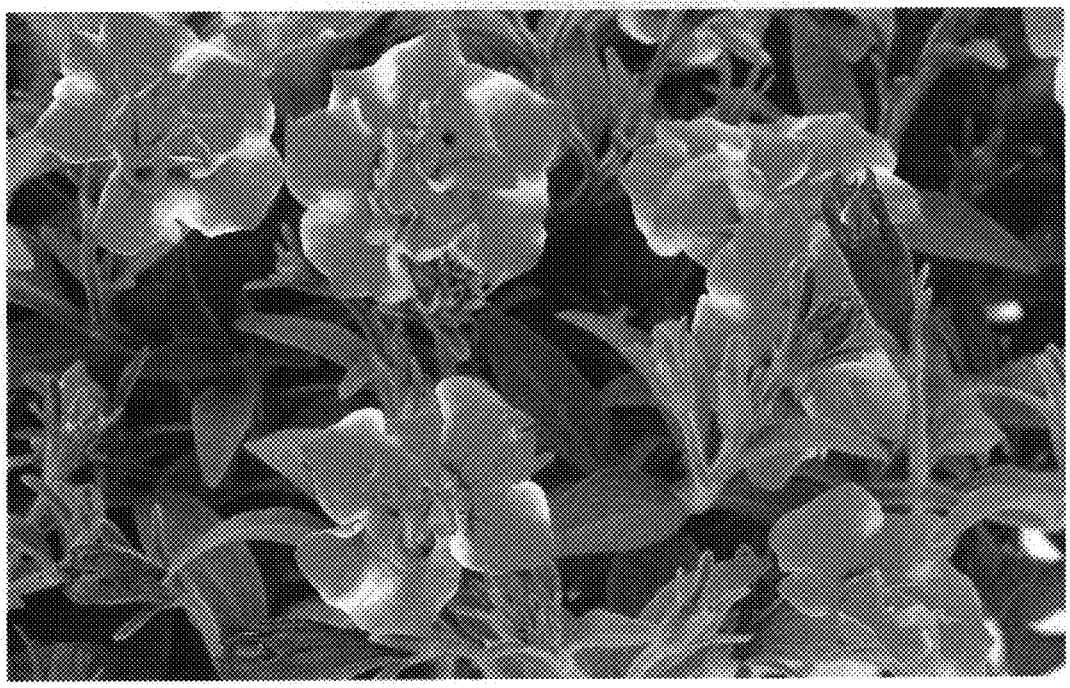

* * * * *